United States Patent
Son et al.

(10) Patent No.: US 8,970,937 B2
(45) Date of Patent: *Mar. 3, 2015

(54) ELECTROCHROMIC MATERIALS AND ELECTROCHROMIC DEVICES USING THE SAME

(75) Inventors: Seung Uk Son, Suwon-si (KR); Chang Ho Noh, Suwon-si (KR); Ji Min Lee, Goyang-si (KR)

(73) Assignee: Samsung Electronics Co., Ltd. (KR)

( * ) Notice: Subject to any disclaimer, the term of this patent is extended or adjusted under 35 U.S.C. 154(b) by 1146 days.

This patent is subject to a terminal disclaimer.

(21) Appl. No.: 12/260,508

(22) Filed: Oct. 29, 2008

(65) Prior Publication Data

US 2009/0251046 A1 Oct. 8, 2009

(30) Foreign Application Priority Data

Apr. 2, 2008 (KR) .................. 10-2008-0030760

(51) Int. Cl.
| | |
|---|---|
| *G02F 1/15* | (2006.01) |
| *C09K 9/02* | (2006.01) |
| *C07C 69/76* | (2006.01) |
| *C07C 69/80* | (2006.01) |
| *C07C 69/92* | (2006.01) |
| *C07C 205/57* | (2006.01) |
| *C07D 333/24* | (2006.01) |

(Continued)

(52) U.S. Cl.
CPC . *C09K 9/02* (2013.01); *C07C 69/76* (2013.01); *C07C 69/80* (2013.01); *C07C 69/92* (2013.01); *C07C 205/57* (2013.01); *C07D 333/24* (2013.01); *C09K 2211/1007* (2013.01); *Y10S 977/932* (2013.01)

USPC ........... 359/265; 313/504; 359/273; 427/164; 549/79; 560/20; 560/95; 977/932

(58) Field of Classification Search
USPC ................ 313/504, 506; 560/95, 20; 549/79; 252/301.16, 582–587; 59/265; 427/164; 977/932; 428/690, 917; 359/265, 273
See application file for complete search history.

(56) References Cited

U.S. PATENT DOCUMENTS

| | | | |
|---|---|---|---|
| 4,340,624 | A | 7/1982 | Yamashita |
| 4,537,826 | A | 8/1985 | Miyamura |
| 4,550,982 | A | 11/1985 | Hirai |

(Continued)

FOREIGN PATENT DOCUMENTS

| | | | | |
|---|---|---|---|---|
| JP | 63-196682 | * | 8/1988 | ............... C09K 9/02 |
| WO | 9735227 | | 9/1997 | |

OTHER PUBLICATIONS

W. Sharmoukh, Kyoung Chul Ko, Ju Hong Ko, Hye Jin Nam, Duk-Young Jung, Changho Noh, Jin Yong Lee, and Seung Uk Son, 5-Substituted isophthalate-based organic electrochromic materials, J. Mater. Chem., 2008, 18, 4408-4413, The Royal Society of Chemistry 2008.*

(Continued)

*Primary Examiner* — Bijan Ahvazi
(74) *Attorney, Agent, or Firm* — Cantor Colburn LLP

(57) ABSTRACT

Disclosed herein are novel electrochromic materials. The electrochromic materials produce various colors. The electrochromic materials can be used to form red electrochromic layers in a simple manner. Therefore, the electrochromic materials are suitable for use in the fabrication of RGB full-color electrochromic devices. Also disclosed herein are electrochromic devices fabricated using the electrochromic materials.

11 Claims, 1 Drawing Sheet

(51) Int. Cl.
*H01J 1/62* (2006.01)
*B05D 5/06* (2006.01)

(56) References Cited

U.S. PATENT DOCUMENTS

| | | | |
|---|---|---|---|
| 6,143,433 A * | 11/2000 | Murata et al. | 428/690 |
| 6,246,508 B1 | 6/2001 | Yde-Andersen | |
| 7,244,864 B2 * | 7/2007 | Anelli et al. | 564/134 |
| 2006/0050357 A1 | 3/2006 | Gavrilov | |
| 2009/0078917 A1 | 3/2009 | Percec | |
| 2009/0097096 A1 * | 4/2009 | Noh et al. | 359/265 |
| 2009/0251046 A1 | 10/2009 | Son | |

OTHER PUBLICATIONS

A.J. Hall, P. Hodge, C.S. McGrail, J. Rickerby, Synthesis of a series of cyclic oligo(alkylidene isophthalate)s by cyclo-depolymerisation, Polymer 41 (2000) 1239-1249, q 1999 Elsevier Science Ltd. All rights reserved.*

Urano et al, "Electrochemical and spectroscopic characteristics fo dimethyl terephthalate," Journal of Materials Chemistry, 2004, vol. 14, pp. 2366-2368.

* cited by examiner

ELECTROCHROMIC MATERIALS AND ELECTROCHROMIC DEVICES USING THE SAME

CROSS-REFERENCE TO RELATED APPLICATION

This application claims priority to Korean Patent Application No. 10-2008-0030760, filed on Apr. 2, 2008, and all the benefits accruing therefrom under 35 U.S.C. §119, the contents of which in its entirety are herein incorporated by reference.

BACKGROUND

1. Field

Disclosed herein is novel electrochromic materials and electrochromic devices fabricated using the electrochromic materials. More specifically, the electrochromic materials produce various colors.

2. Description of the Related Art

Electrochromism is the phenomenon displayed by some chemical species which have a reversibly changeable color when a voltage is applied thereto. A material capable of undergoing reversible changes of optical properties by the electrochemical redox reaction accompanying such electrochromic properties is called an electrochromic material. That is, the electrochromic material may not have a color in the absence of an electric field and then may display a certain color when an electric field is applied, e.g., by an external source, and vice versa.

Electrochromic devices taking advantage of such an electrochromic phenomenon have various advantages such as high reflectivity without a need for an external light source, excellent flexibility and portability, and the feasibility of weight reduction, and are therefore expected to have promising applications for various flat-panel displays ("FPDs"). In particular, electrochromic devices are receiving a great deal of attention, due to high applicability to E-paper which is recently under intensive research and study, as an electronic medium capable of replacing paper.

Examples of the electrochromic materials may include inorganic compounds such as tungsten oxides, molybdenum oxides, and the like, and organic compounds such as pyridine, aminoquinone and azine compounds. However, even though blue and green electrochromic materials are known in such a nano-electrochromic type, red electrochromic materials are not yet known.

In comparison with inorganic electrochromic materials, organic electrochromic materials are disadvantageous in terms of long-term stability, but have advantages in that they are applicable to flexible substrates and can be used to form thin films by wet processing. Based on these advantages, a great deal of research has been conducted on organic electrochromic materials.

On the other hand, a combination of red, green and blue is required to achieve full-color electrochromic devices. However, few red electrochromic materials have been discovered to date. Under such circumstances, there exists a need to develop red electrochromic materials.

SUMMARY

Disclosed herein is a novel electrochromic material represented by the following Formula 1:

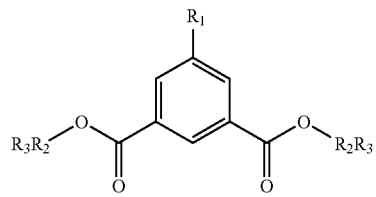

FORMULA (1)

wherein R1 is selected from the group consisting of a hydrogen atom, a halogen atom, a hydroxyl group, an amino group, a cyano group, a nitro group, a carboxyl group, a benzoylamino group, a $C_1$-$C_{50}$ alkylsulfonylamino group, a $C_1$-$C_{50}$ linear alkyl group, a $C_1$-$C_{50}$ branched alkyl group, a $C_1$-$C_{50}$ cyclic alkyl group, a $C_2$-$C_{50}$ linear alkenyl group, a $C_2$-$C_{50}$ branched alkenyl group, a $C_2$-$C_{50}$ linear alkynyl group, a $C_2$-$C_{50}$ branched alkynyl group, a $C_1$-$C_{50}$ alkoxy group, a $C_2$-$C_{50}$ alkylalkoxy group, a $C_6$-$C_{50}$ aryl group, a $C_5$-$C_{50}$ heteroaryl group and a thienyl group, wherein the branched alkyl group, the cyclic alkyl group, the branched alkenyl group, the aryl group and the heteroaryl group is unsubstituted or substituted with at least one group selected from halo, hydroxyl, amino, cyano, nitro, thienyl, $C_1$-$C_7$ alkyl and $C_2$-$C_7$ alkenyl groups, wherein each $R_2$ is —$(CH_2)_m$—, wherein m is an integer from 1 to 10, and wherein each $R_3$ is selected from the group consisting of —CH=$CH_2$, a $C_1$-$C_{10}$ linear alkyl group, a $C_1$-$C_{10}$ branched alkyl group, a $C_1$-$C_{10}$ cyclic alkyl group, a $C_2$-$C_{10}$ linear alkenyl group, a $C_2$-$C_{10}$ branched alkenyl group, a $C_6$-$C_{12}$ aryl group, and a $C_5$-$C_{12}$ heteroaryl group.

In one exemplary embodiment, the electrochromic material produces a particular color.

Also disclosed herein is an exemplary embodiment of electrochromic device including a transparent electrode, an opposite electrode disposed substantially opposite to the transparent electrode and an electrochromic layer interposed between the transparent and opposite electrodes, wherein the electrochromic layer contains the electrochromic material.

In one exemplary embodiment, the electrochromic device can be fabricated in a simple manner.

BRIEF DESCRIPTION OF THE DRAWINGS

The exemplary embodiments will be more clearly understood from the following detailed description taken in conjunction with the accompanying drawings, where.

DETAILED DESCRIPTION OF EMBODIMENTS

Figure 1:
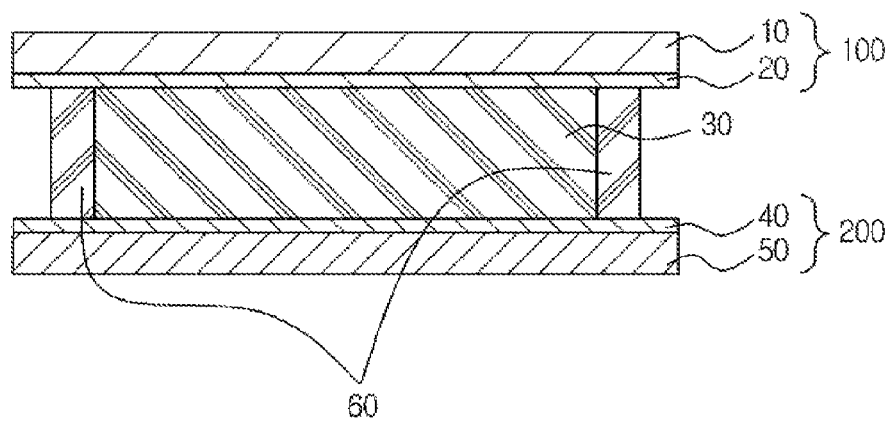
FIG. 1 is a schematic cross-sectional view illustrating the structure of an exemplary embodiment of an electrochromic device.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on, the other element or intervening elements may be present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to cross section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention. Hereinafter, exemplary embodiments of the present invention will be described in detail with reference to the accompanying drawings.

According to one exemplary embodiment, there is provided an electrochromic material represented by Formula 1:

FORMULA (1)

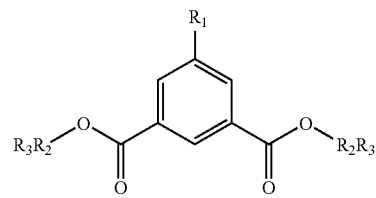

wherein $R_1$ is selected from the group consisting of a hydrogen atom, a halogen atom, a hydroxyl group, an amino group, a cyano group, a nitro group, a carboxyl group, a benzoylamino group, a $C_1$-$C_{50}$ alkylsulfonylamino group, a $C_1$-$C_{50}$ linear alkyl group, a $C_1$-$C_{50}$ branched alkyl group, a $C_1$-$C_{50}$ cyclic alkyl group, a $C_2$-$C_{50}$ linear alkenyl group, a $C_2$-$C_{50}$ branched alkenyl group, a $C_2$-$C_{50}$ linear alkynyl group, a $C_2$-$C_{50}$ branched alkynyl group, a $C_1$-$C_{50}$ alkoxy group, a $C_2$-$C_{50}$ alkylalkoxy group, a $C_6$-$C_{50}$ aryl group, a $C_5$-$C_{50}$ heteroaryl group and a thienyl group, wherein the branched alkyl group, the cyclic alkyl group, the branched alkenyl group, the aryl group or the heteroaryl group may be unsubstituted or substituted with at least one group selected from the group consisting of halo, hydroxyl, amino, cyano, nitro, thienyl, $C_1$-$C_7$ alkyl and $C_2$-$C_7$ alkenyl groups, wherein each $R_2$ is —$(CH_2)_m$—, wherein m is an integer from 1 to 10, and wherein each $R_3$ is —$CH=CH_2$, a $C_1$-$C_{10}$ linear alkyl group, a $C_1$-$C_{10}$ branched alkyl group, a $C_1$-$C_{10}$ cyclic alkyl group, a $C_2$-$C_{10}$ linear alkenyl group, a $C_2$-$C_{10}$ branched alkenyl group, a $C_6$-$C_{12}$ aryl group, and a $C_5$-$C_{12}$ heteroaryl group.

In one exemplary embodiment, $R_1$ in Formula 1 may be a hydrogen atom, a halogen atom, a nitro group, a $C_1$-$C_3$ alkyl group, a $C_1$-$C_3$ alkoxy group, a phenyl group unsubstituted or substituted with at least one group selected from the group consisting of a halo group in the ortho-position, a halo group in the meta-position, a halo group in the para-position, an alkoxy group in the ortho-position, an alkoxy group in the meta-position, an alkoxy group in the para-position, a phenyl group in the ortho-position, a phenyl group in the meta-position, a phenyl group in the para-position, and a thienyl group.

In one exemplary embodiment, the compound of Formula 1 can be synthesized by refluxing a solution of a corresponding substituted or unsubstituted isophthalic acid derivative in thionyl chloride and adding 5-hexen-1-ol thereto.

Exemplary embodiments of the electrochromic material can be selected from the group consisting of, but not necessarily limited to, the compounds represented by Formulae 2 to 10:

FORMULA (2)

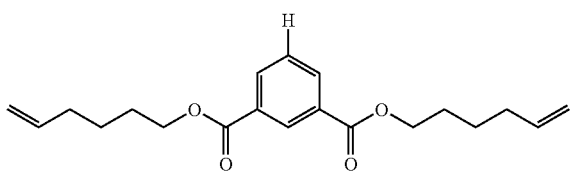

FORMULA (3)

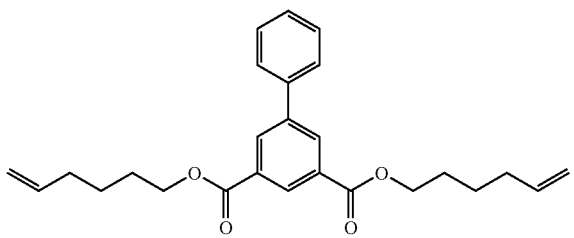

FORMULA (4)

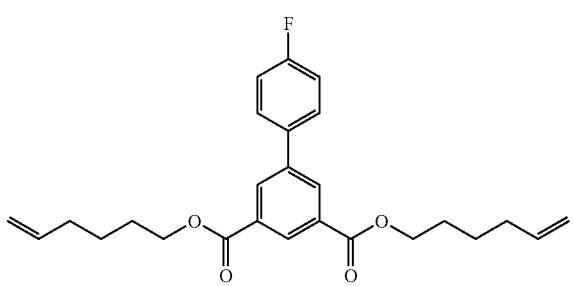

FORMULA (5)

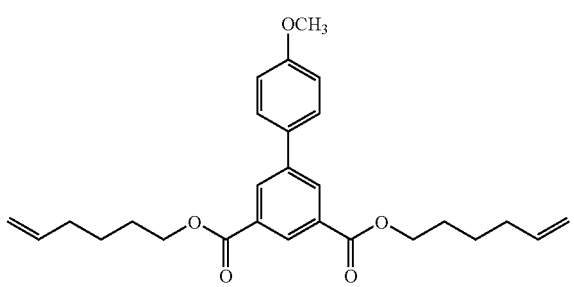

FORMULA (6)

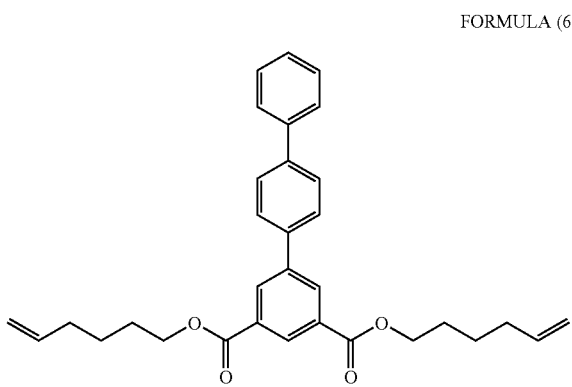 [SMILES: C=CCCCCOC(=O)c1cc(C(=O)OCCCCC=C)cc(-c2ccc(-c3ccccc3)cc2)c1]

FORMULA (7)

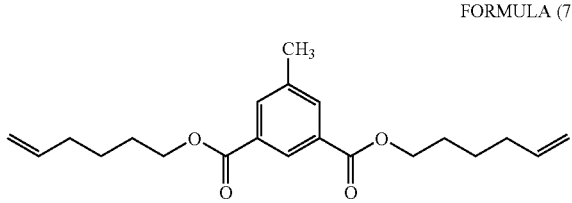

FORMULA (8)

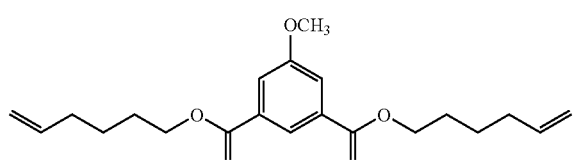

FORMULA (9)

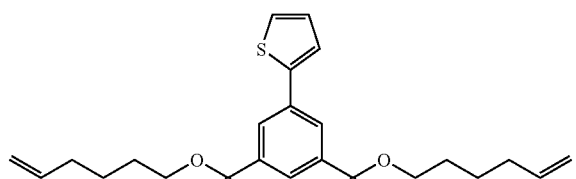

FORMULA (10)

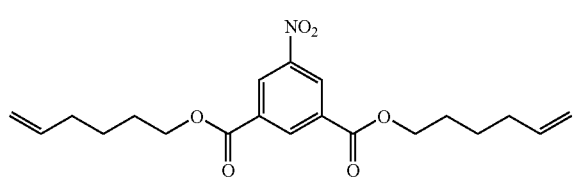

In one exemplary embodiment, the compound of Formula 2, 7, 8 or 10 can be synthesized by refluxing a solution of a corresponding substituted or unsubstituted isophthalic acid derivative in thionyl chloride and adding 5-hexen-1-ol thereto, as depicted in Reaction 1:

Reaction (1)

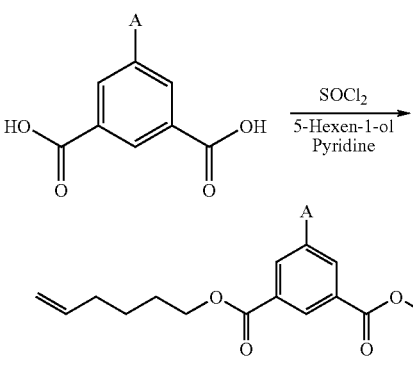

wherein R is selected from the group consisting of H, CH₃, OCH₃ and NO₂.

In one exemplary embodiment, the compound of Formula 3, 4, 5, 6 or 9 can be synthesized by coupling the compound of Formula 11 as a starting material with an arylboronic acid, as depicted in Reaction 2:

Formula (11)

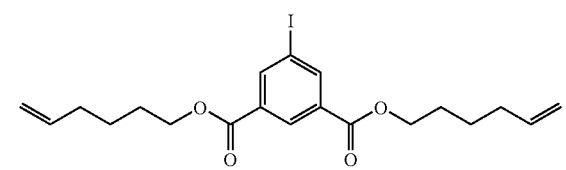

-continued
Reaction (2)

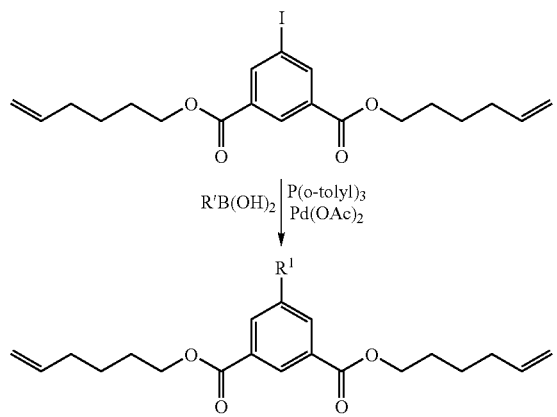

wherein R' is selected from the group consisting of a phenyl, 4-fluorophenyl, 4-methoxyphenyl, 4,4'-biphenyl and 2-thienyl group.

In accordance with another exemplary embodiment, there is provided an electrochromic device including a transparent electrode and an opposite electrode disposed substantially opposite to each other and an electrochromic layer interposed between the pair of electrodes wherein the electrochromic layer contains the electrochromic material.

It would be apparent to one of ordinary skill in the art that the electrochromic device can be fabricated by any suitable well-known method with the exception that the electrochromic layer is formed using the above-described exemplary embodiment of an electrochromic material.

FIG. 1 is a schematic cross-sectional view of an exemplary embodiment of an electrochromic device according to the present invention. Referring to FIG. 1, the electrochromic device has a structure in which a pair of electrodes, including a transparent electrode 100 and an opposite electrode 200, are disposed substantially opposite to each other and an electrochromic layer 30 is interposed between the pair of electrodes.

The transparent electrode 100 includes a transparent substrate 10 and a conductive film 20, and the opposite electrode 200, which is disposed substantially opposite to the transparent electrode 100, consists of a conductive film 40 and a transparent substrate 50. Spacers 60 are disposed between the transparent electrode 100 and the opposite electrode 200 to maintain a cell gap therebetween.

In one exemplary embodiment, the electrochromic layer 30 may be formed using a solution of the electrochromic material in an electrolyte. In such an exemplary embodiment, any of several well-known materials may be used as the electrolyte, and specific exemplary embodiments thereof include, but are not limited to, solutions of lithium salts, potassium salts and sodium salts in suitable solvents as would be apparent to one of ordinary skill in the art. More specifically, in one exemplary embodiment the electrolyte may be a solution of tetrabutylammonium hexafluorophosphate or a solution of $LiClO_4$, but the present invention is not necessarily limited thereto.

The conductive films 20 and 40 of the respective transparent electrode 100 and the opposite electrode 200 may function as an anode and a cathode. A voltage applied between the transparent electrode 100 and the opposite electrode 200 allows the electrochromic material to react with ions and electrons present in the electrolyte, resulting in a change in the color of the electrochromic material.

According to one exemplary embodiment, the electrochromic device may turn yellow in response to a voltage applied thereto when the device contains the electrochromic material of Formula 2:

FORMULA (2)

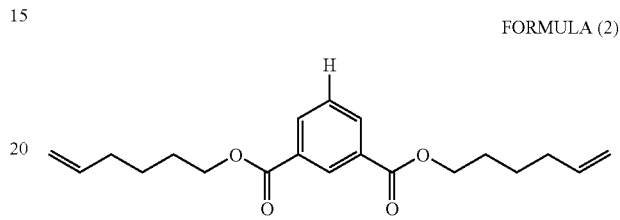

The electrochromic device may turn pink in response to a voltage applied thereto when the device contains the electrochromic material of Formula 3:

FORMULA (3)

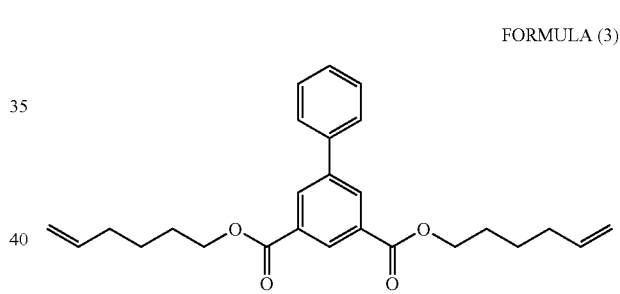

The electrochromic device may turn red in response to a voltage applied thereto when the device contains the electrochromic material of Formula 4:

FORMULA (4)

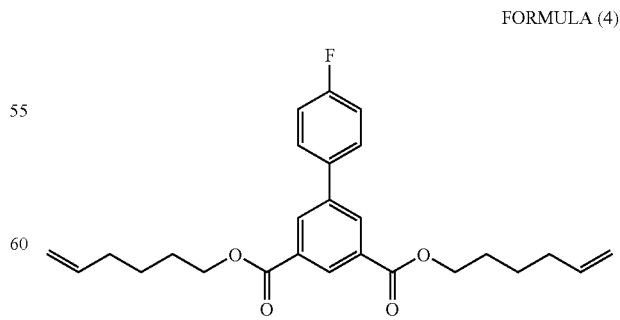

The electrochromic device may turn pink in response to a voltage applied thereto when the device contains the electrochromic material of Formula 5:

FORMULA (5)

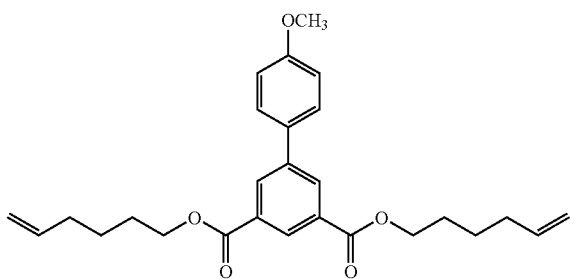

The electrochromic device may turn violet in response to a voltage applied thereto when the device contains the electrochromic material of Formula 6:

FORMULA (6)

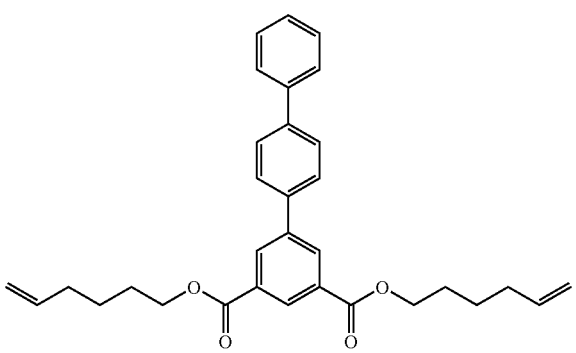

The electrochromic device may turn reddish-orange in response to a voltage applied thereto when the device contains the electrochromic material of Formula 7:

FORMULA (7)

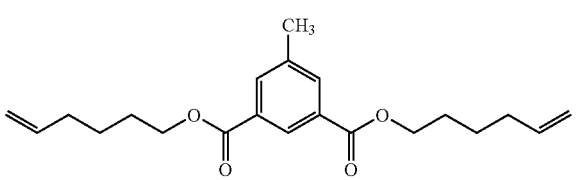

The electrochromic device may turn yellow in response to a voltage applied thereto when the device contains the electrochromic material of Formula 8:

FORMULA (8)

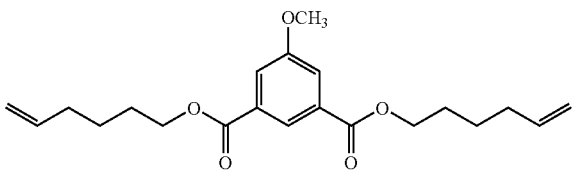

The electrochromic device may turn red in response to a voltage applied thereto when the device contains the electrochromic material of Formula 9:

FORMULA (9)

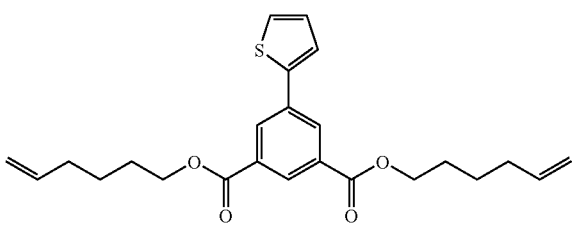

On the other hand, the electrochromic device may produce one or more colors in response to the intensity of a voltage applied thereto when the device contains the electrochromic material of Formula 10:

FORMULA (10)

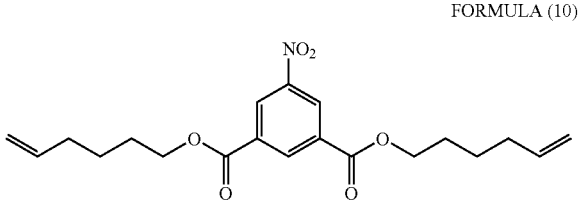 [SMILES: C=CCCCCOC(=O)c1cc(C(=O)OCCCCC=C)cc([N+](=O)[O-])c1]

Specifically, the electrochromic device containing the electrochromic material of Formula 11 may turn blue at a voltage of about 4.0 V to about 4.5 V and red at a voltage of about 4.8 V to about 5.3 V.

Non-limiting exemplary embodiments of the transparent substrates 10 and 50 include transparent inorganic substrates, exemplary embodiments of which include glass and quartz substrates, and transparent plastic substrates, exemplary embodiments of which include polyethylene terephthalate ("PET"), polyethylene naphthalate ("PEN"), polycarbonate, polystyrene and polypropylene substrates. Exemplary embodiments also include configurations having flexible substrates.

As would be apparent to one of ordinary skill in the art, a transparent conductive material can be coated on the transparent substrates 10 and 50 to form the conductive films 20 and 40, respectively, and the composition thereof is not particularly limited. Specific exemplary embodiments thereof include, but are not necessarily limited to, indium tin oxide ("ITO"), fluorine-doped tin oxide ("FTO") and conductive polymers, e.g., polyphenylacetylene and polythiophene.

Furthermore, in one exemplary embodiment a counter material layer may be formed on the conductive film 40 of the opposite electrode 200 in terms of efficient electrochemical reactions of the electrochromic material. Exemplary embodiments of suitable counter materials include, but are not necessarily limited to, antimony-doped tin oxide ("ATO") and indium tin oxide ("ITO").

The material used to form the conductive film 40 of the opposite electrode 200 is not otherwise limited so long as it is conductive.

A more detailed description of exemplary embodiments will be described in more detail with reference to the following examples. However, these examples are given merely for the purpose of illustration and are not to be construed as limiting the scope of the embodiments.

EXAMPLES

Preparation of Electrochromic Materials

Preparative Example 1

Synthesis of Isophthalate Derivative

In the first example, 6.0 mmol of isophthalic acid was dissolved in 3 mL (41 mmol) of $SOCl_2$ in a 50 mL Schlenk flask. The reaction mixture was heated for 3 hours under reflux at 76° C. Subsequently, the solution was cooled to room temperature and the excess $SOCl_2$ was removed under vacuum. As used herein, "room temperature" is used to denote a certain range of temperatures within an enclosed space at which humans are accustomed, one example of the range being from about 22° C. to about 28° C., however the term is not limited thereto. The oily product was dried under vacuum for one hour. Next, 20 mL of methylene chloride was added to dissolve the oily product. Then, 2.16 mL (18 mmol) of 5-hexen-1-ol and 1.94 mL (24 mmol) of pyridine were added at 0° C. The reaction mixture was stirred for 3 hours at 0° C. After reaction, the reaction mixture was extracted using methylene chloride and an aqueous $NH_4Cl$ solution. The filtered solution was dried using $MgSO_4$ and evaporated. The product was separated via column chromatography using a mixture of hexane and ether (in a 12:2 ratio) as an eluent. The eluate was dried under vacuum to afford Compound of Formula 2:

FORMULA (2)

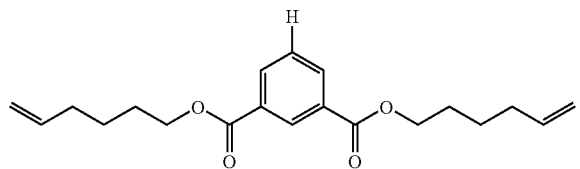

$^1$H NMR data for Compound of Formula 2 are as follows.
$^1$H NMR (300 MHz, $CDCl_3$): δ (ppm)=8.67 (s, 1H), 8.21 (d, J=7.8 Hz, 2H), 7.52 (t, J=7.5 Hz, 1H), 5.80 (m, 2H), 5.03 (d, J=14 Hz, 2H), 4.96 (d, J=6.9 Hz, 2H), 4.34 (t, J=6.6 Hz, 4H), 2.12 (q, J=6.9 Hz, 4H), 1.79 (q, J=6.9 Hz, 4H), 1.54 (q, J=6.9 Hz, 4H).

Preparative Example 2

Synthesis of Isophthalate Derivative

The procedure of Preparative Example 1 was repeated except that 5-iodoisophthalic acid was used instead of isophthalic acid to prepare the compound of Formula 11:

FORMULA (11)

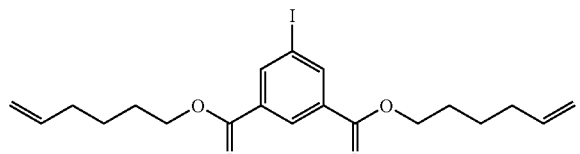

Then, 0.22 mmol of the compound of Formula 9, 29 mg (0.24 mmol) of phenylboronic acid, 5.0 mg (0.022 mmol) of palladium acetate, 0.15 g (1.1 mmol) of potassium carbonate and 13.3 mg (0.044 mmol) of tritolyl phosphine were added to 20 mL of DMF. The reaction mixture was heated at 90° C. for 4 hours. After reaction, the reaction mixture was extracted using methylene chloride and an aqueous $NH_4Cl$ solution and then, dried using $MgSO_4$. The product was separated via column chromatography using hexane/ether (12:1) eluent. The eluate was dried under vacuum to afford Compound of Formula 3:

FORMULA (3)

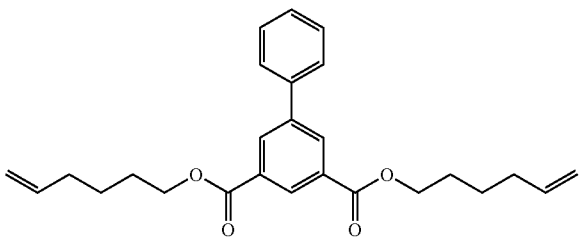

$^1$H NMR data for Compound of Formula 3 are as follows.
$^1$H NMR (300 MHz, $CDCl_3$): δ (ppm)=8.65 (s, 1H), 8.45 (s, 2H), 7.66 (d, J=6.9 Hz, 2H), 7.47 (m, 3H), 5.82 (m, 2H), 5.06 (d, J=14 Hz, 2H), 4.97 (d, J=6.9 Hz, 2H), 4.41 (t, J=6.6 Hz, 4H), 2.14 (q, J=6.9 Hz, 4H), 1.83 (q, J=6.9 Hz, 4H), 1.55 (q, J=6.9 Hz, 4H).

Preparative Example 3

Synthesis of Isophthalate Derivative

FORMULA (4)

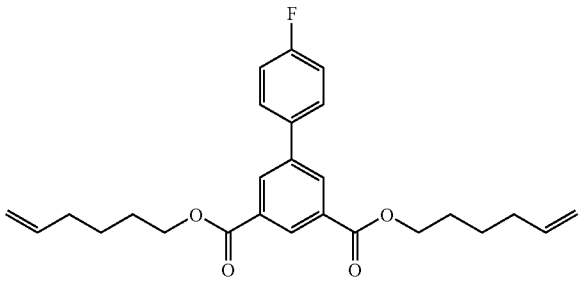

Compound of Formula 4 was prepared in the same manner as in Preparative Example 2 except that 4-fluorophenylboronic acid was used instead of phenylboronic acid. $^1$H NMR data for Compound of Formula 4 are as follows.

$^1$H NMR (300 MHz, $CDCl_3$): δ (ppm)=8.64 (s, 1H), 8.39 (s, 2H), 7.62 (d, J=8.7 Hz, 2H), 7.17 (t, J=8.7 Hz, 2H), 5.83 (m, 2H), 5.04 (d, J=14 Hz, 2H), 4.98 (d, J=6.9 Hz, 2H), 4.39 (t, J=6.6 Hz, 4H), 2.14 (q, J=7.2 Hz, 4H), 1.84 (q, J=6.9 Hz, 4H), 1.58 (q, J=6.9 Hz, 4H).

Preparative Example 4

Synthesis of Isophthalate Derivative

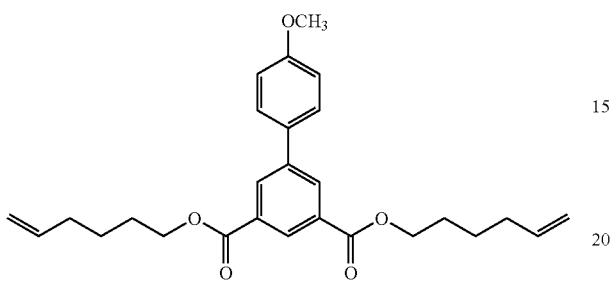

FORMULA (5)

Compound of Formula 5 was prepared in the same manner as in Preparative Example 2 except that 4-methoxyphenylboronic acid was used instead of phenylboronic acid. $^1$H NMR data for Compound of Formula 5 are as follows.

$^1$H NMR (300 MHz, CDCl$_3$): δ (ppm)=8.60 (s, 1H), 8.41 (s, 2H), 7.61 (d, J=6.9 Hz, 2H), 7.00 (d, J=6.9 Hz, 2H), 5.81 (m, 2H), 5.04 (d, J=15 Hz, 2H), 4.99 (d, J=7.0 Hz, 2H), 4.40 (t, J=6.9 Hz, 4H), 3.86 (s, 3H), 2.15 (q, J=6.9 Hz, 4H), 1.84 (q, J=6.9 Hz, 4H), 1.59 (q, J=7.2 Hz, 4H).

Preparative Example 5

Synthesis of Isophthalate Derivative

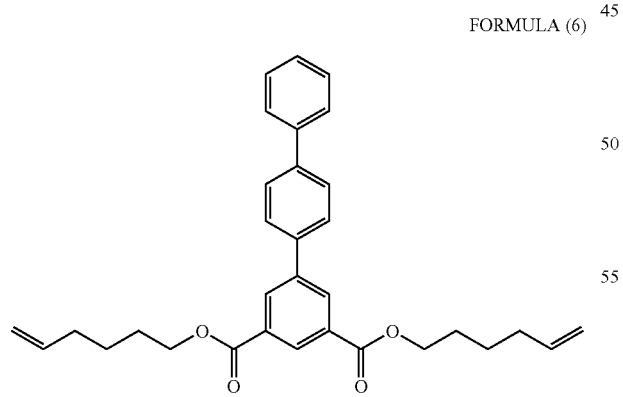

FORMULA (6)

Compound of Formula 6 was prepared in the same manner as in Preparative Example 2 except that 4,4'-biphenylboronic acid was used instead of phenylboronic acid. $^1$H NMR data for Compound of Formula 6 are as follows.

$^1$H NMR (300 MHz, CDCl$_3$): δ (ppm)=8.66 (s, 1H), 8.51 (s, 2H), 7.74 (s, 4H), 7.65 (d, J=7.5 Hz, 2H), 7.48 (t, J=7.2 Hz, 2H), 7.40 (t, J=7.2 Hz, 1H), 5.84 (m, 2H), 5.05 (d, J=14 Hz, 2H), 4.98 (d, J=6.9 Hz, 2H), 4.40 (t, J=6.6 Hz, 4H), 2.15 (q, J=7.2 Hz, 4H), 1.84 (q, J=7.2 Hz, 4H), 1.57 (q, J=7.2 Hz, 4H).

Preparative Example 6

Synthesis of Isophthalate Derivative

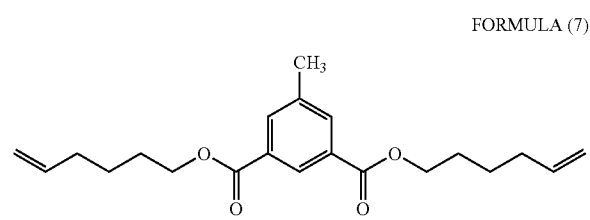 [SMILES: C=CCCCCOC(=O)c1cc(C)cc(C(=O)OCCCCC=C)c1]

FORMULA (7)

Compound of Formula 7 was prepared in the same manner as in Preparative Example 1 except that 5-methylisophthalic acid was used instead of isophthalic acid. $^1$H NMR data for Compound of Formula 7 are as follows.

$^1$H NMR (300 MHz, CDCl$_3$): δ (ppm)=8.47 (s, 1H), 8.02 (s, 2H), 5.81 (m, 2H), 5.01 (d, J=15 Hz, 2H), 4.96 (d, J=6.9 Hz, 2H), 4.32 (t, J=6.9 Hz, 4H), 2.45 (s, 3H), 2.14 (q, J=6.9 Hz, 4H), 1.80 (q, J=6.9 Hz, 4H), 1.53 (q, J=6.9 Hz, 4H).

Preparative Example 7

Synthesis of Isophthalate Derivative

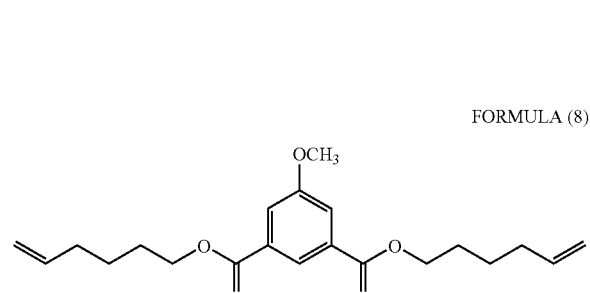

FORMULA (8)

Compound of Formula 8 was prepared in the same manner as in Preparative Example 1 except that 5-methoxyisophthalic acid was used instead of isophthalic acid. $^1$H NMR data for Compound of Formula 8 are as follows.

$^1$H NMR (300 MHz, CDCl$_3$): δ (ppm)=8.26 (s, 1H), 7.73 (s, 2H), 5.82 (m, 2H), 5.03 (d, J=14 Hz, 2H), 4.97 (d, J=6.9 Hz, 2H), 4.36 (t, J=6.6 Hz, 4H), 3.88 (s, 3H), 2.12 (q, J=6.9 Hz, 4H), 1.79 (q, J=6.9 Hz, 4H), 1.54 (q, J=6.9 Hz, 4H).

Preparative Example 8

Synthesis of Isophthalate Derivative

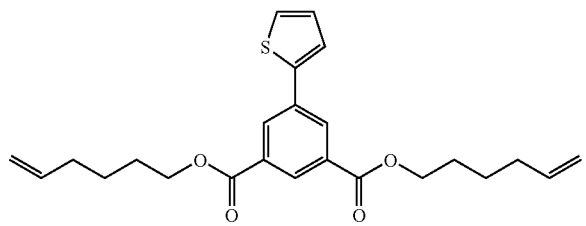

FORMULA (9)

Compound of Formula 9 was prepared in the same manner as in Preparative Example 2 except that 2-thienylboronic acid was used instead of phenylboronic acid. $^1$H NMR data for Compound of Formula 9 are as follows.

$^1$H NMR (300 MHz, CDCl$_3$): δ (ppm)=8.56 (s, 1H), 8.43 (s, 2H), 7.46 (d, J=3.6 Hz, 1H), 7.36 (d, J=5.1 Hz, 1H), 7.12 (dd, J=3.6, 5.0 Hz, 1H), 5.84 (m, 2H), 5.07 (d, J=14 Hz, 2H), 4.98 (d, J=6.9 Hz, 2H), 4.40 (t, J=6.6 Hz, 4H), 2.14 (q, J=6.9 Hz, 4H), 1.84 (q, J=6.9 Hz, 4H), 1.57 (q, J=6.9 Hz, 4H).

Preparative Example 9

Synthesis of Isophthalate Derivative

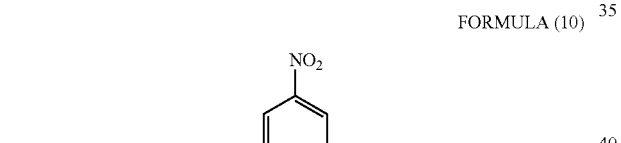

FORMULA (10)

Compound of Formula 10 was prepared in the same manner as in Preparative Example 1 except that 5-nitroisophthalic acid was used instead of isophthalic acid. $^1$H NMR data for Compound of Formula 10 are as follows.

$^1$H-NMR (300 MHz, CDCl$_3$): δ (ppm)=8.99 (s, 2H), 8.93 (s, 1H), 5.79 (m, 2H), 5.04 (d, J=14 Hz, 2H), 4.95 (d, J=6.9 Hz, 2H), 4.38 (t, J=6.9 Hz, 4H), 2.14 (q, J=7.0 Hz, 4H), 1.79 (q, J=6.9 Hz, 4H), 1.54 (q, J=6.9 Hz, 4H).

[Fabrication of Electrochromic Devices]

Examples 1-9

Each of the electrochromic materials prepared in Preparative Examples 1-9 was dissolved in γ-butyrolactone solution containing 0.2 M anhydrous tetrabutylammonium hexafluorophosphate to prepare a 0.225 M electrochromic solution. Subsequently, spacers were disposed between two ITO-coated glass substrates to maintain a cell gap, followed by sealing of an internal chamber formed between the two ITO-coated glass substrates. The electrochromic solution was injected into the cell via syringe to fabricate an electrochromic test device.

Examples 10-18

Each of the electrochromic materials prepared in Preparative Examples 1-9 was mixed with 3.33 g (30 mmol) of 1-vinyl-2-pyrrolidinone, 0.031 g (0.2 mmol) of N,N'-methylenebisacrylamide, 0.99 g (10 mmol) of 1-methyl-2-pyrrolidinone, 4.6 mg (0.02 mmol) of ammonium persulfate, 1.2 mg (0.01 mmol) of N,N,N',N'-tetramethylethylenediamine and 0.068 g (0.2 mmol) of tetrabutylammonium hexafluorophosphate to prepare a 0.225 M electrochromic solution in order to form Examples 10-18, respectively. Subsequently, spacers were disposed between two ITO-coated glass substrates to maintain a cell gap, followed by sealing of an internal chamber formed between the two ITO-coated glass substrates. The electrochromic solution was injected into the cell via syringe, and thermally treated at 70° C. for 12 hours to fabricate an electrochromic test device containing the electrochromic material in the form of a gel.

[Characterization of Electrochromic Devices]

Color changes in the electrochromic devices fabricated in Examples 1-18 were observed when the respective voltages indicated in Table 1 were applied to the devices. The results are shown in Table 1.

TABLE 1

| Example No. | Applied voltage (V) | Color |
|---|---|---|
| 1 | 5.05 | Yellow |
| 2 | 4.11 | Pink |
| 3 | 5.20 | Red |
| 4 | 4.5 | Pink |
| 5 | 4.38 | Violet |
| 6 | 5.32 | Reddish-orange |
| 7 | 5.21 | Yellow |
| 8 | 5.5 | Red |
| 9 | 4.17 | Blue |
|  | 5.19 | Red |
| 10 | 5.05 | Yellow |
| 11 | 4.11 | Pink |
| 12 | 5.20 | Red |
| 13 | 4.5 | Pink |
| 14 | 4.38 | Violet |
| 15 | 5.32 | Reddish-orange |
| 16 | 5.21 | Yellow |
| 17 | 5.5 | Red |
| 18 | 4.17 | Blue |
|  | 5.19 | Red |

As apparent from the results in Table 1, the exemplary embodiments of the example electrochromic devices, each of which includes an electrochromic layer in the form of a solution or gel formed using the corresponding novel isophthalate derivative, produced various colors, e.g., red as well as blue and yellow colors.

Figure 2:
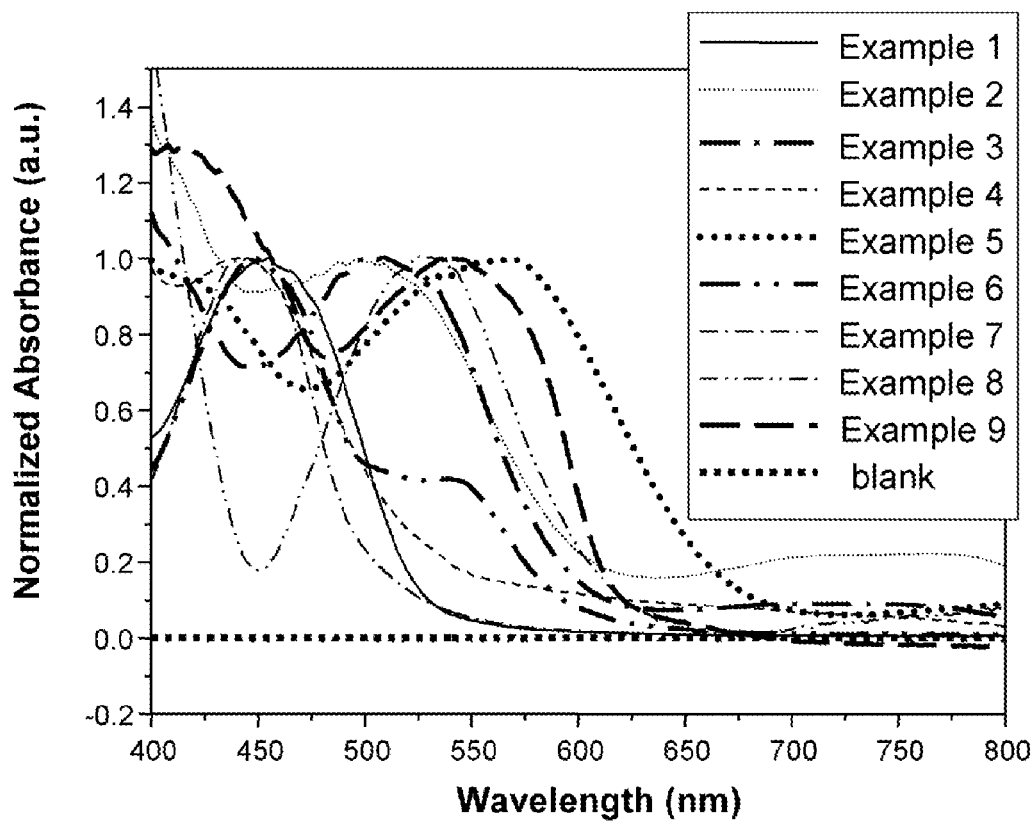
FIG. 2 shows UV spectra of constituent electrochromic materials of exemplary embodiments of electrochromic devices fabricated according to Examples 1 to 9 after the colors of the devices were changed in response to voltages applied to the devices.

On the other hand, after a voltage was applied to each of the electrochromic devices fabricated in Examples 1-9 to change the color of the device, a UV spectrum of the constituent electrochromic material of the device was obtained using a spectrometer (USB4000, Ocean Optics). The results are shown in FIG. 2. The spectra of FIG. 2 reveal that the constituent electrochromic materials of the devices fabricated in Examples 1-9 showed peaks at wavelengths of 450 nm, 509 nm, 510 nm, 449 nm, 562 nm, 448 nm, 446 nm, 530 nm and 544 nm, respectively, corresponding to red as well as yellow and violet colors.

In addition, the results in Table 1 show that the novel electrochromic material prepared in Preparative Example 9 produced various colors in response to the intensity of a voltage applied thereto. Specifically, the electrochromic material was colorless when no voltage was applied thereto (a), turned blue at a voltage of 4.17 V, and turned red at a voltage of 5.19 V.

Although exemplary embodiments have been described herein with reference to the foregoing embodiments, those skilled in the art will appreciate that various modifications and changes are possible without departing from the spirit of the invention as disclosed in the accompanying claims. Therefore, it is to be understood that such modifications and changes are encompassed within the scope of the invention.

What is claimed is:

1. An electrochromic material represented by the following Formula (1):

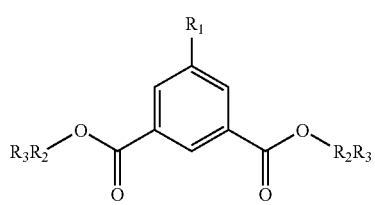

FORMULA (1)

wherein $R_1$ is selected from the group consisting of a halogen atom, a cyano group, a carboxyl group, a benzoylamino group, a $C_1$-$C_{50}$ alkylsulfonylamino group, a $C_1$-$C_{50}$ linear alkyl group, a $C_1$-$C_{50}$ branched alkyl group, a $C_1$-$C_{50}$ cyclic alkyl group, a $C_2$-$C_{50}$ linear alkenyl group, a $C_2$-$C_{50}$ branched alkenyl group, a $C_2$-$C_{50}$ linear alkynyl group, a $C_2$-$C_{50}$ branched alkynyl group, a $C_1$-$C_{50}$ alkoxy group, a $C_2$-$C_{50}$ alkylalkoxy group, a $C_6$-$C_{50}$ aryl group, a $C_5$-$C_{50}$ heteroaryl group, and a thienyl group, wherein the branched alkyl group, the cyclic alkyl group, and the branched alkenyl group is unsubstituted or substituted with at least one group selected from the group consisting of halo, hydroxyl, amino, cyano, nitro, thienyl, $C_1$-$C_7$ alkyl and $C_2$-$C_7$ alkenyl groups, wherein the aryl group and the heteroaryl group are unsubstituted or substituted with at least one group selected from the group consisting of halo, hydroxyl, amino, cyano, nitro, thienyl, alkoxy, phenyl, $C_1$-$C_7$ alkyl and $C_2$-$C_7$ alkenyl groups, wherein each $R_2$ is —$(CH_2)_m$—, wherein m is an integer from 1 to 10, and wherein each $R_3$ is selected from the group consisting of —CH=CH$_2$, a $C_1$-$C_{10}$ linear alkyl group, a $C_1$-$C_{10}$ branched alkyl group, a $C_1$-$C_{10}$ cyclic alkyl group, a $C_2$-$C_{10}$ linear alkenyl group, a $C_2$-$C_{10}$ branched alkenyl group, a $C_6$-$C_{12}$ aryl group, and a $C_5$-$C_{12}$ heteroaryl group.

2. The electrochromic material of claim 1, wherein $R_1$ is selected from the group consisting of a halogen atom, a $C_1$-$C_3$ alkyl group, a $C_1$-$C_3$ alkoxy group, a phenyl group unsubstituted or substituted with at least one group selected from the group consisting of a halo group in the ortho-position, a halo group in the meta-position, a halo group in the para-position, an alkoxy group in the ortho-position, an alkoxy group in the meta-position, an alkoxy group in the para-position, a phenyl group in the ortho-position, a phenyl group in the meta-position, a phenyl group in the para-position, and a thienyl group.

3. The electrochromic material of claim 1, wherein the electrochromic material is selected from the group consisting of the compounds represented by Formulae 3, 4, 5, 6, 7, 8 and 9, wherein the Formulae 3-9 are:

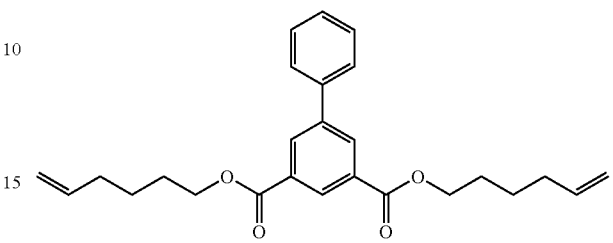

FORMULA (3)

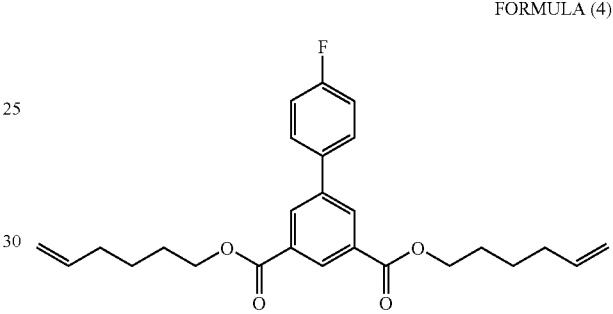

FORMULA (4)

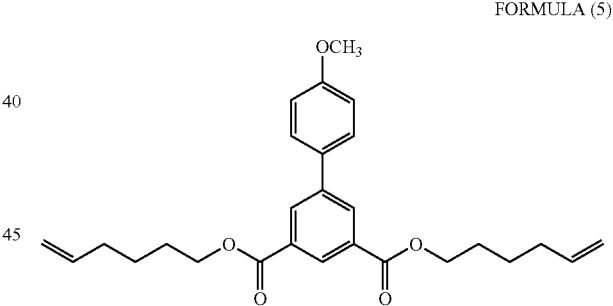

FORMULA (5)

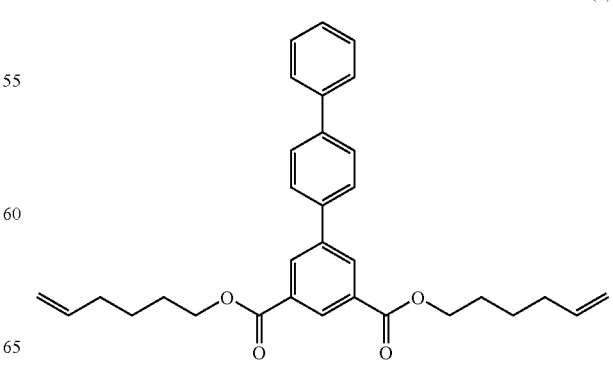

FORMULA (6)

FORMULA (7)

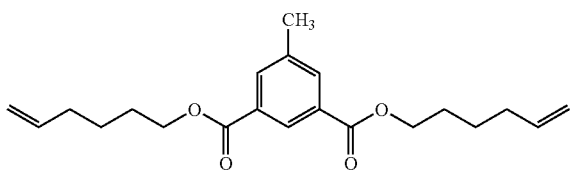

FORMULA (8)

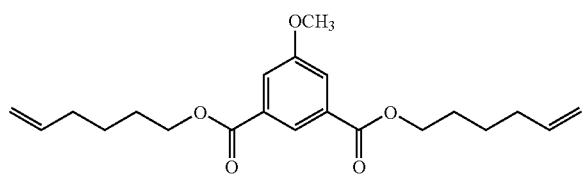

FORMULA (9)

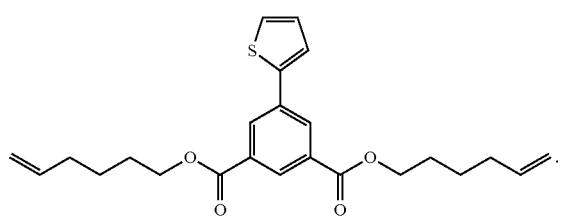

4. An electrochromic device comprising:

a transparent electrode;

an opposite electrode disposed substantially opposite to the transparent electrode; and an electrochromic layer interposed between the transparent electrode and the opposite electrode, wherein the electrochromic layer contains the electrochromic material of claim 1.

5. The electrochromic device of claim 4, wherein the electrochromic device displays a pink color in response to a voltage applied thereto when the device contains the electrochromic material of Formula 3:

FORMULA (3)

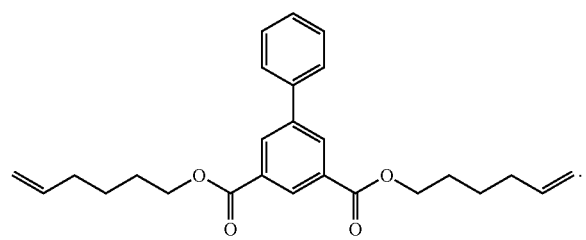

6. The electrochromic device of claim 4, wherein the electrochromic device displays a red color in response to a voltage applied thereto when the device contains the electrochromic material of Formula 4:

FORMULA (4)

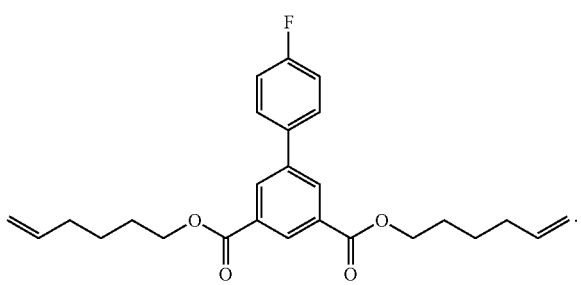

7. The electrochromic device of claim 4, wherein the electrochromic device displays a pink color in response to a voltage applied thereto when the device contains the electrochromic material of Formula 5:

FORMULA (5)

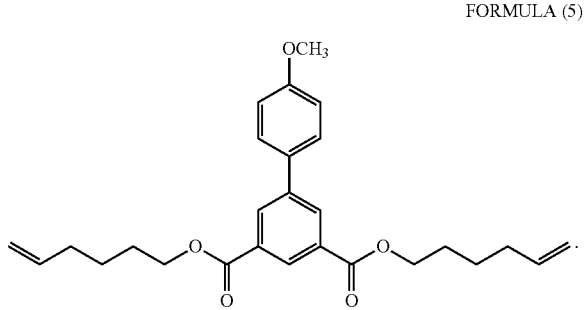

8. The electrochromic device of claim 4, wherein the electrochromic device displays a violet color in response to a voltage applied thereto when the device contains the electro chromic material of Formula 6:

FORMULA (6)

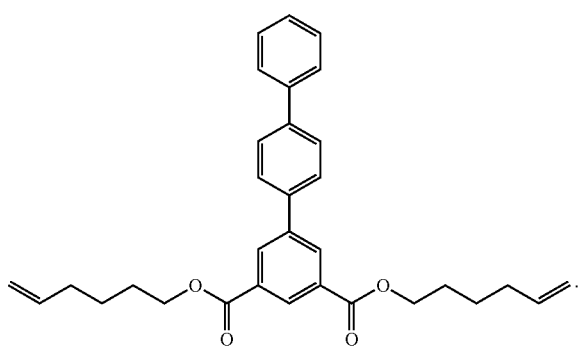

9. The electrochromic device of claim 4, wherein the electrochromic device displays a reddish-orange color in response to a voltage applied thereto when the device contains the electro chromic material of Formula 7:

FORMULA (7)

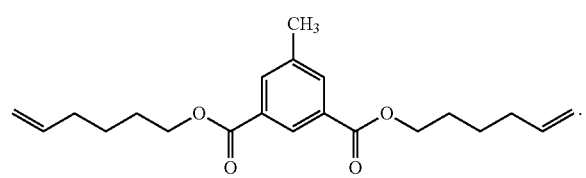

10. The electrochromic device of claim 4, wherein the electrochromic device displays a yellow color in response to a voltage applied thereto when the device contains the electrochromic material of Formula 8:

FORMULA (8)

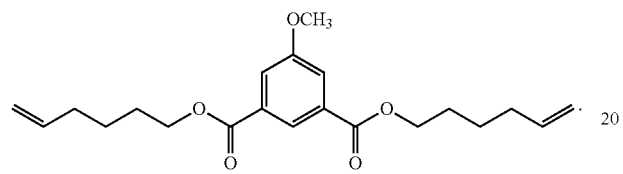

11. The electrochromic device of claim 4, wherein the electrochromic device displays a red color in response to a voltage applied thereto when the device contains the electrochromic material of Formula 9:

FORMULA (9)

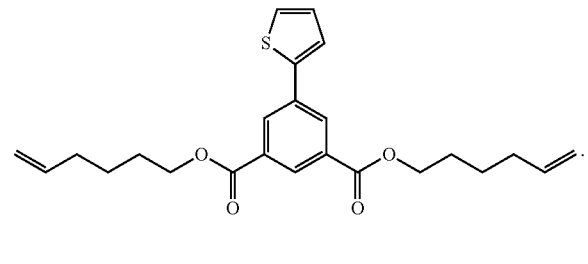

* * * * *